(12) United States Patent
Katane et al.

(10) Patent No.: US 9,974,814 B2
(45) Date of Patent: May 22, 2018

(54) GAS FILLED DECELLULARIZED MATRIX

(71) Applicant: Miromatrix Medical Inc., Eden Prairie, MN (US)

(72) Inventors: Aleksandr Katane, Eden Prairie, MN (US); Dominique Seetapun, Minnetonka, MN (US); Jeffrey Ross, Chaska, MN (US)

(73) Assignee: Miromatrix Medical Inc., Eden Prairie, MN (US)

( * ) Notice: Subject to any disclaimer, the term of this patent is extended or adjusted under 35 U.S.C. 154(b) by 0 days. days.

(21) Appl. No.: 15/079,985

(22) Filed: Mar. 24, 2016

(65) Prior Publication Data

US 2016/0279170 A1 Sep. 29, 2016

Related U.S. Application Data

(60) Provisional application No. 62/138,850, filed on Mar. 26, 2015.

(51) Int. Cl.

| | |
|---|---|
| *A61N 1/02* | (2006.01) |
| *A61K 35/42* | (2015.01) |
| *A61K 35/22* | (2015.01) |
| *A61K 35/30* | (2015.01) |
| *A61K 35/34* | (2015.01) |
| *A61K 35/38* | (2015.01) |
| *A61K 35/39* | (2015.01) |
| *A61K 35/407* | (2015.01) |
| *A61K 45/06* | (2006.01) |
| *A61K 47/02* | (2006.01) |
| *A01N 1/02* | (2006.01) |
| *A61L 27/36* | (2006.01) |
| *A61L 27/38* | (2006.01) |
| *A61L 27/54* | (2006.01) |

(52) U.S. Cl.
CPC .............. *A61K 35/42* (2013.01); *A01N 1/021* (2013.01); *A01N 1/0289* (2013.01); *A61K 35/22* (2013.01); *A61K 35/30* (2013.01); *A61K 35/34* (2013.01); *A61K 35/38* (2013.01); *A61K 35/39* (2013.01); *A61K 35/407* (2013.01); *A61K 45/06* (2013.01); *A61K 47/02* (2013.01); *A61L 27/3633* (2013.01); *A61L 27/3683* (2013.01); *A61L 27/3691* (2013.01); *A61L 27/38* (2013.01); *A61L 27/54* (2013.01); *A61L 2300/414* (2013.01); *A61L 2300/426* (2013.01)

(58) Field of Classification Search
None
See application file for complete search history.

(56) References Cited

U.S. PATENT DOCUMENTS

| | | | |
|---|---|---|---|
| 2011/0011410 A1 | 1/2011 | Desai et al. | |
| 2015/0182560 A1* | 7/2015 | Calle | ..................... A61K 35/42 424/93.7 |
| 2016/0030638 A1* | 2/2016 | Ross | ................... C12N 5/0671 424/93.7 |

FOREIGN PATENT DOCUMENTS

| | | |
|---|---|---|
| WO | WO-2011/066522 A2 | 6/2011 |
| WO | WO-2014/013241 A1 | 1/2014 |
| WO | WO-2014/059316 A1 | 4/2014 |
| WO | WO-2016/154447 A1 | 9/2016 |

OTHER PUBLICATIONS

"International Application Serial No. PCT/US2016/024032, International Search Report dated Aug. 26, 2016", 5 pgs.
"International Application Serial No. PCT/US2016/024032, Written Opinion dated Aug. 26, 2016", 8 pgs.
Ladhoff, Juliane, et al., "Immune privilege of endotheial cells diffrerentiated from endothelial progenitor cells", *Cardiovascular Research*, 88, (2010), 121-129.
"International Application Serial No. PCT/US2016/024032, International Preliminary Report on Patentability dated Oct. 5, 2017", 10 pgs.

\* cited by examiner

*Primary Examiner* — Ralph J Gitomer
(74) *Attorney, Agent, or Firm* — Schwegman Lundberg & Woessner, P.A.

(57) ABSTRACT

A method to provide an inflated decellularized extracellular matrix of a mammalian organ or a vascularized portion thereof, or a mammalian vascularized tissue or a vascularized portion thereof, an inflated decellularized extracellular matrix of a mammalian organ or a vascularized portion thereof, or a mammalian vascularized tissue or a vascularized portion thereof, and uses thereof, are provided.

21 Claims, 9 Drawing Sheets
(9 of 9 Drawing Sheet(s) Filed in Color)

GAS FILLED DECELLULARIZED MATRIX

CROSS-REFERENCE TO RELATED APPLICATIONS

This application claims the benefit of the filing date of U.S. application Ser. No. 62/138,850, filed on Mar. 26, 2015, the disclosure of which is incorporated by reference herein.

BACKGROUND

The extracellular matrix (ECM) is a complex network of structural and functional proteins that form tissue-specific architectures. The ECM includes secreted products of resident cells in each tissue and organ. The matrix molecules include structural and functional proteins, glycoproteins, and glycosaminoglycans. The resident cells of the ECM, besides produce ECM, receive signals therefrom, allowing for tissue development and/or homeostasis. Those properties are the basis for the use of ECM-based materials in tissue engineering and regenerative medicine. Because ECM provides a naturally occurring and highly conserved substrate for cell viability and growth that has reduced immunogenicity, ECM-based substrates having individual ECM components or of whole decellularized tissues have been used in a wide range of applications in both preclinical and clinical settings.

SUMMARY OF THE INVENTION

The invention provides a gas filled (inflated) decellularized extracellular matrix of a mammalian organ or vascularized portion thereof, or a vascularized mammalian tissue or a portion thereof. In one embodiment, the three dimensional decellularized extracellular matrix retains the shape of the original organ or portion thereof, or tissue or portion thereof. In one embodiment, the extracellular matrix after inflation has a height that is greater than about 0.2 cm up to about 0.6 cm, e.g., about 0.3 cm to about 0.5 cm, including about 0.4 cm, relative to that of a corresponding uninflated extracellular matrix. For example, the extracellular matrix of a liver lobe of a large mammal after inflation has a height that is greater than about 0.3 cm to about 0.5 cm, including about 0.4 cm, relative to that a corresponding uninflated extracellular matrix of a liver lobe. In one embodiment, the extracellular matrix after inflation has a height that is increased by at least 25% up to 1000%, e.g., at least 50% up to about 500% or about 75% up to about 250%, relative to a corresponding uninflated extracellular matrix. In one embodiment, the gas filled decellularized extracellular matrix of an organ or tissue has a shape, size or volume that is about 25% to 125%, for example, about 50% to about 150% or about 75% to about 110%, that of the corresponding native organ or tissue. The active introduction of a gas, for instance a vapor (a gas having particles or droplets), into a decellularized extracellular matrix of an organ or tissue via its natural vasculature or any other conduit, e.g., duct or cavity, provides for a gas filled decellularized extracellular matrix of an organ or tissue matrix that is expanded relative to its non-inflated shape, and in some embodiments has the original shape of the native (cellularized) organ or tissue prior to decellularization. The shape of the gas filled decellularized extracellular matrix, for example one filled with air, is retained as a result of the gas being trapped within the tissue or organ and filling the spaces originally occupied by cells. In one embodiment, the gas is retained in the extracellular matrix in the absence of a seal. The product is a three dimensional decellularized extracellular matrix that can be used for but is not limited to implantation as surgical mesh, surgical filler, void fillers, tissue engineering, and the like. Inflation allows the matrix to open up by filling the compartments where cells used to occupy, thus allowing for the matrix to be easily cut because it becomes more rigid. Likewise, the opening of the matrix by introduction of a gas allows it to be more easily morsalized when it is frozen.

In one embodiment, the gas comprises normal air, $CO_2$, argon, nitrogen, or oxygen, or any combination thereof. In one embodiment, the gas comprises an aerosolized drug, e.g., one or more steroids, antibiotics or antifungals. In one embodiment, the vapor component comprises a sterilization agent such as periacetic acid or hydrogen peroxide, or a carrier, such as phosphate buffered saline, lactose, glucose or liposome carriers, or a nebulizer type vapor, having various drugs or proteins including but not limited to one or more antibiotics, steroids, or anti-fungals, or proteins such as VEGF, FGF-2, EGF, PDGF, IGF, or HGF, or micro- or nano-particles comprising proteins, small molecules or drugs.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1:
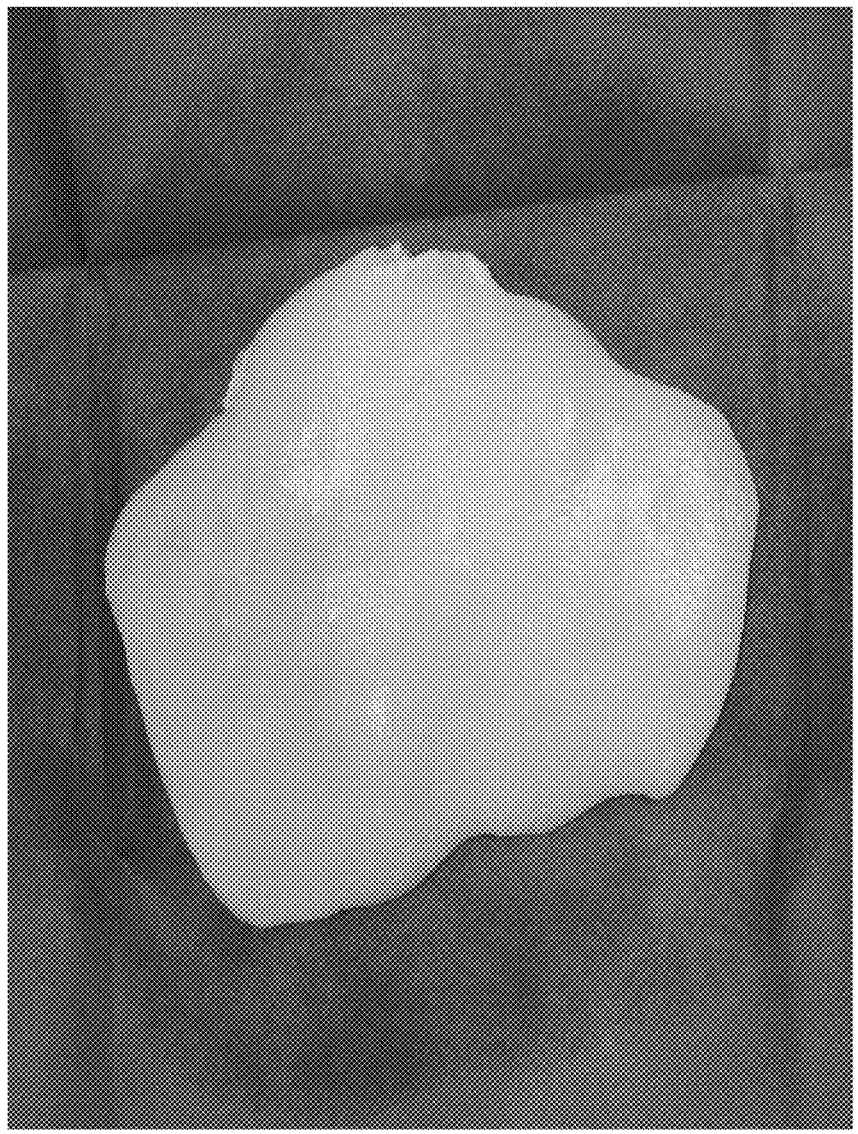
FIG. 1. Image of a decellularized extracellular matrix of a liver lobe before inflation.
Figure 2:
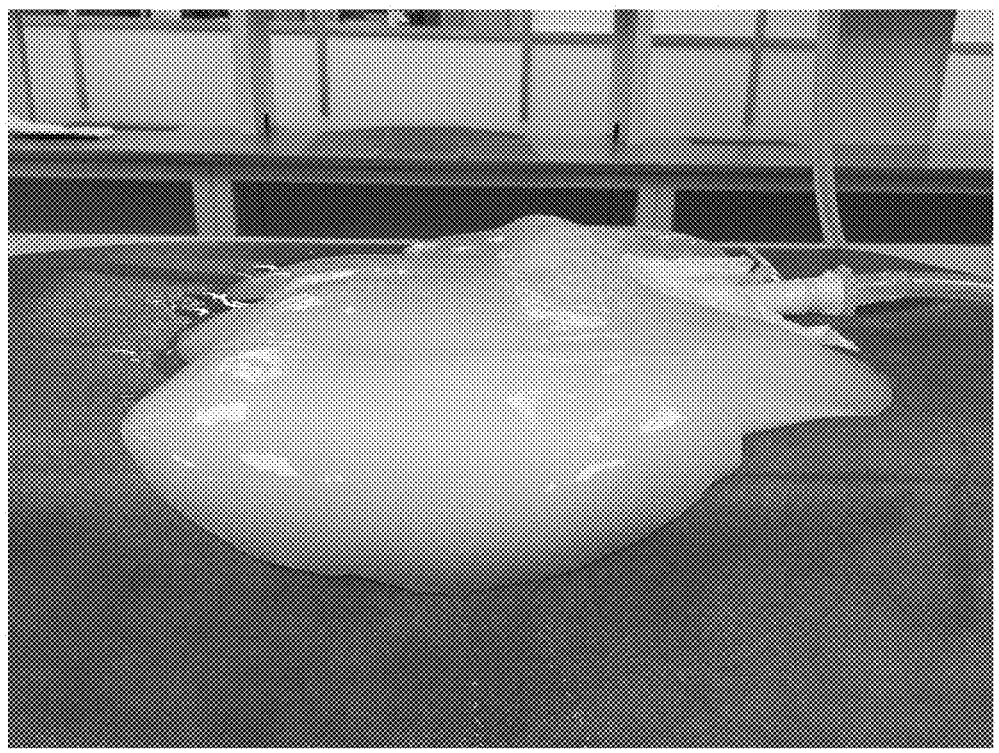
FIG. 2. Image of a decellularized extracellular matrix of a cannulated liver before inflation.
Figure 3:
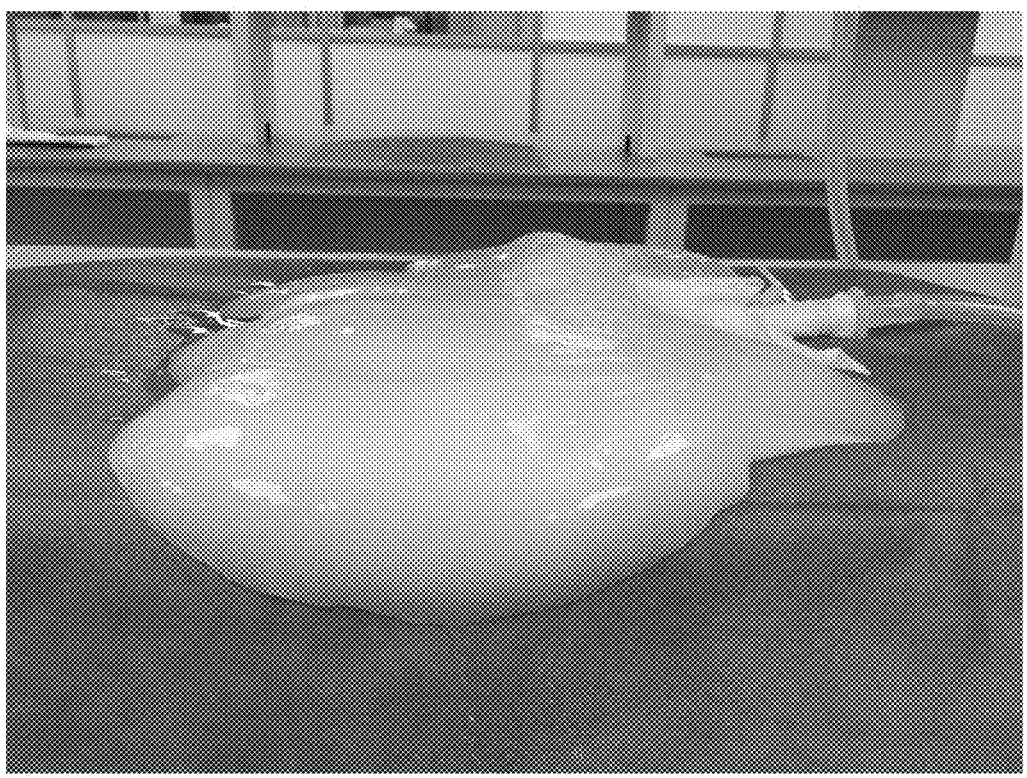
FIG. 3. Image of a decellularized extracellular matrix of a cannulated liver during inflation.
Figure 4:
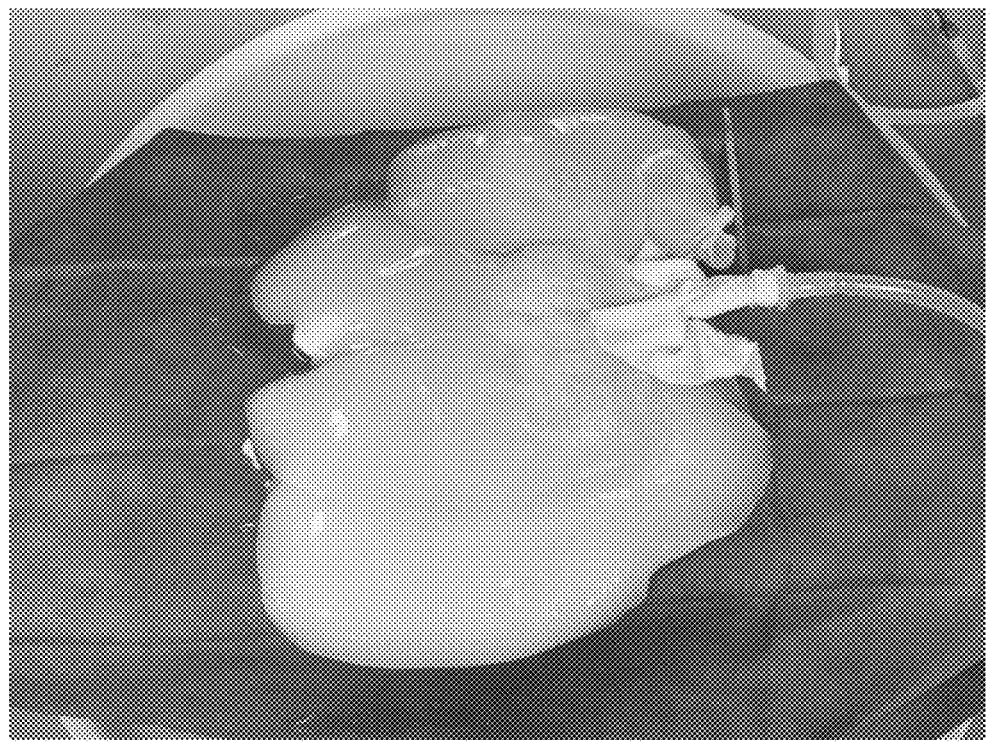
FIG. 4. Image of a decellularized extracellular matrix of a cannulated liver during inflation and taken after the image in FIG. 3.
Figure 5:
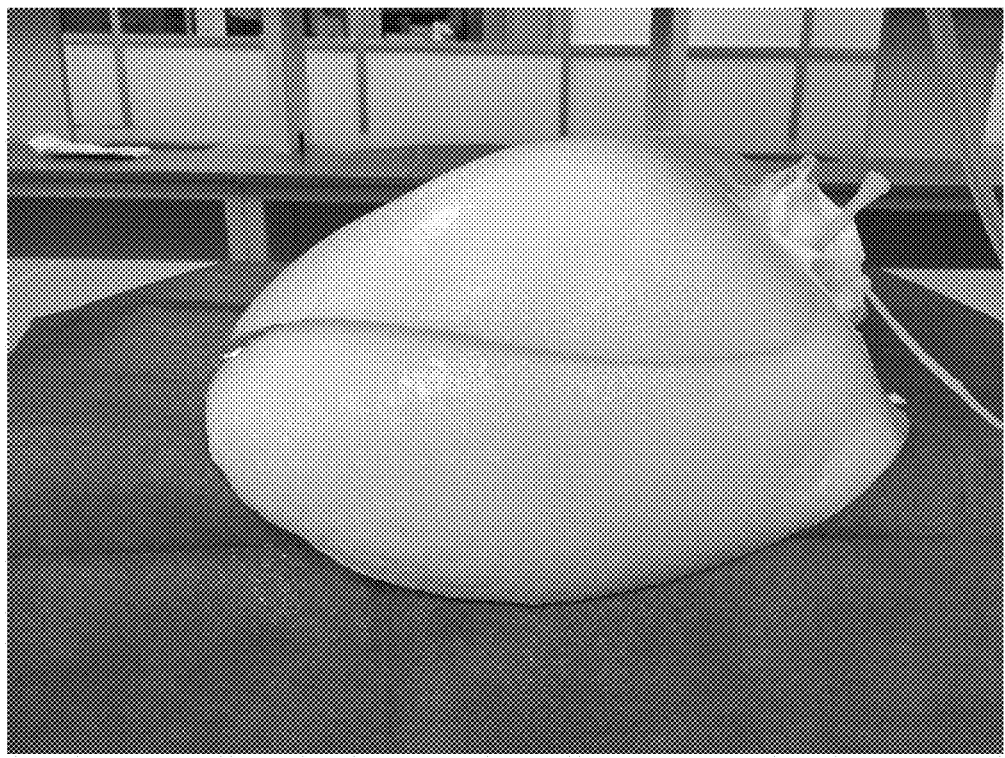
FIG. 5. Image of a decellularized extracellular matrix of a cannulated liver during and taken after the image in FIG. 4.
Figure 6:
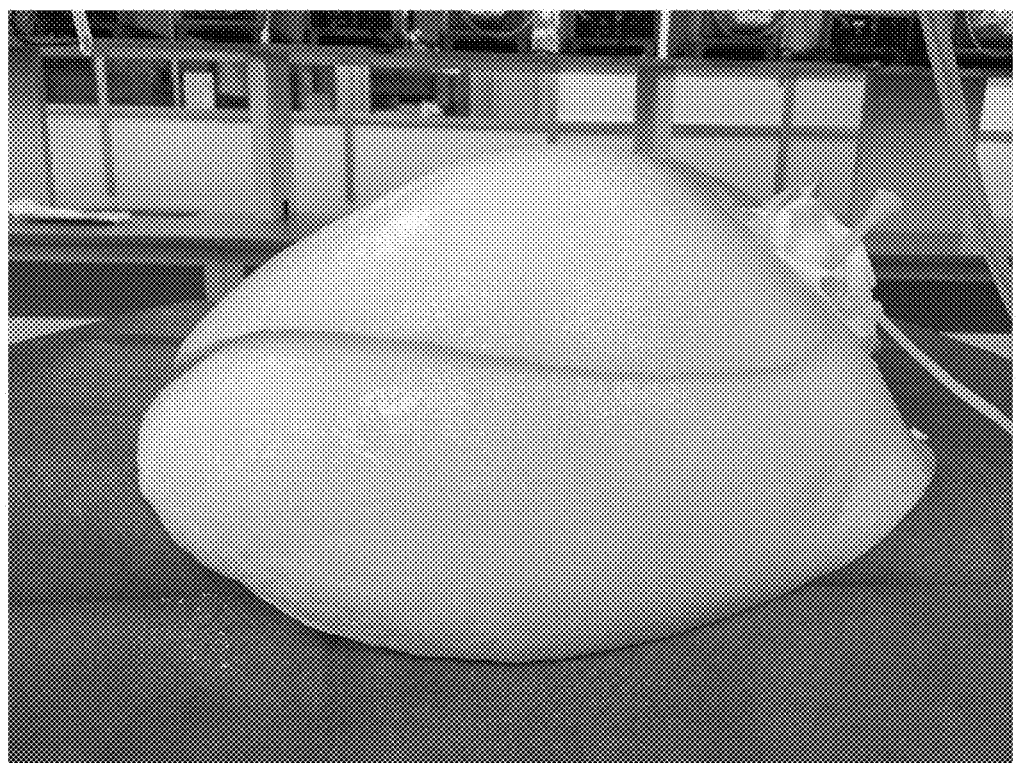
FIG. 6. Image of a decellularized extracellular matrix of a cannulated liver during and taken after the image in FIG. 5.

Decellularization results in an acellular tissue or organ that has extracellular matrix. The resulting space that was originally occupied by cells is occupied by the decellularization solution or whatever solution the tissue is in. In tissues and organs such as liver, lung, muscle, spleen and heart that contain a high ratio of cells compared to extracellular matrix, e.g., a ratio of 1:3 to 1:20 depending on the type of tissue, the original shape of the organ or tissue is reduced as compartments that once contained the cells collapse. While the original shape of the organ or tissue can be maintained if it is perfused under pressure, but once removed from that, the organ or tissue will deflate as the fluid slowly drains out. To create a three dimensional matrix that maintains the original shape, size or volume of the organ or tissue, a gas or a gas including particles or droplets (vapor) is introduced to at least one a vessel duct or cavity of the decellularized organ or tissue to fill the void spaces resulting in a three dimensional matrix that can be cut, shaped and/or modeled for various uses without collapsing of the compartment(s) where cells used to reside.

Thus, the invention provides, in one embodiment, active access to the vascular network of a decellularized organ or tissue. This can be accomplished by cannulating, directly injecting into the ECM or use of a positive displacement device, and optionally sealing any main vein or artery belonging to the decellularized organ or tissue. In some embodiments, other vascular channels may be blocked off to create a more closed vascular system. In one embodiment, a pump, syringe, pressurized gas, canned gas and/or a canister containing a gas or a vapor comprising one or more proteins, small molecules, drugs or other agents, is used to actively introduce a gas or a vapor, including for example applying a vacuum outside the tissue to cause distribution of introduced gases and/or vapors, for instances at pump rates, e.g., about 10 to about 10,000 mL/min and pressures from about 1 to about 200 mmHg, into the decellularized organ or tissue through tubing, cannulas, connectors, needles and/or syringes connected to a cannulated arterial or venous vessel. The gas or vapor is pumped at a determined rate, e.g., 2,000 mL/min, until desired results are achieved, e.g., as determined visually or via physical measurements, for instance, filling to a defined volume or volumetric shape, increased surface tension and/or increased back pressure. The gas or vapor in the inflated organ or tissue becomes trapped in the cellular compartments and remains there.

The gas or vapor filled decellularized organ or tissue matrix can be employed in various therapeutic applications including the use of the whole decellularized organ or tissue, or portions of the organ or tissue, e.g., useful as surgical fillers, surgical mesh, fillers for fistulas and other voids, and to prepare granular or morsalized pieces of the decellularized ECM of the organ or tissue. Morsels are about 0.5 mm to about 10 mm in diameter; granules are < about 0.5 mm in diameter. Morsal production may include grating the expanded ECM and then running the pieces through a series of strainers to achieve the desired size range of morsels. Granule production may include grinding the grated pieces down into smaller pieces and then running them through a series of even smaller strainers to achieve the desired granule size range. Alternatively, the decellularized ECM of the organ or tissue may be seeded with any type of cell or any combination of cells.

In one embodiment, the gas inflated (expanded) decellularized matrix is used as a shape retaining surgical filler. In one embodiment, the gas inflated decellularized matrix is used for the use in treatment of fistula. In one embodiment, the gas inflated decellularized matrix is subjected to e-beam sterilization, e.g., to set the protein conformation of the matrix thereby increasing the retention of its shape. In one embodiment, the gas used to inflate the decellularized matrix sterilizes the decellularized matrix. The inflation of the decellularized matrix allows for ease of cutting desired three dimensional portions of the matrix, ease of cryodessicating and/or morsalizing the decellularized matrix for wound applications. In one embodiment, the decellularized matrix is inflated with a vapor, or after an initial inflation with a non-particle containing, non-droplet containing gas exposed to a vapor, having one or more drugs, e.g., one or more cytokines or growth factors to induce remodeling in vivo and/or to increase cellular engraftment when seeded with cells. In one embodiment, the decellularized matrix is inflated with a vapor containing one or more small molecules or proteins, or after an initial inflation with a non-particle containing, non-droplet containing gas exposed to a vapor, having one or more drugs, to be slowly released in-vivo acting as controlled delivery vehicle, carrier or device.

Figure 7:
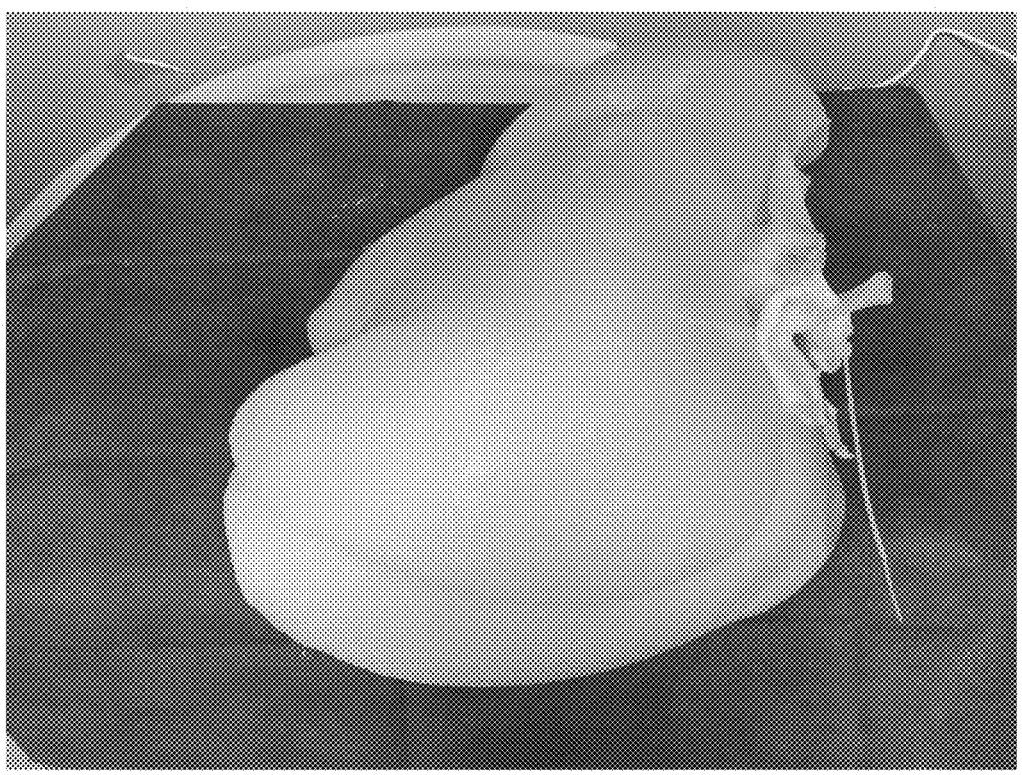
FIG. 7. Side image of decellularized extracellular matrix of a liver during inflation.
Figure 8:
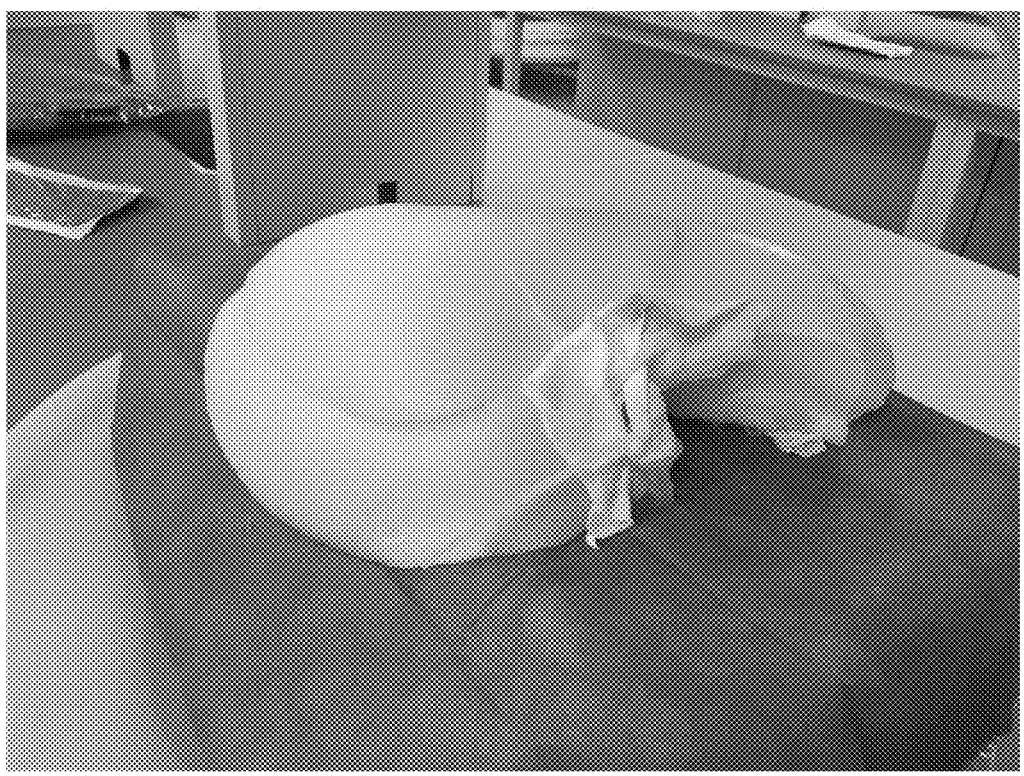
FIG. 8. Side image of decellularized extracellular matrix of a liver during inflation.
Figure 9:
FIG. 9. Side image of decellularized extracellular matrix of a liver during inflation.

FIGS. 2-6 show the gradual inflation of a decellularized liver with air. FIGS. 7-9 show that the inflated liver retains its shape independent of active pressure. The ability to section the inflated matrix is also demonstrated by the cross sections of the inflated liver lobe.

Exemplary Sources of Organs and Tissues for Decellularized ECM

A tissue is a group of cells with a common structure and function, e.g., epithelial tissue, connective tissue, muscle tissue (skeletal, cardiac, or smooth muscle), and nervous tissue, and includes a pliable sheet that covers or lines or connects organs. An organ is a collection of tissues (two or more) joined in structural unit to serve a common function. Organs include but are not limited to the brain, liver, pancreas, bone, spleen, heart, stomach, kidney, lungs, whole muscles, thymus, anus, and intestine. As used herein, an organ includes perfusable whole organs, or parts of an organ, or vascularized structures thereof, and a tissue includes any structures that contain vascularized tissues, e.g., a trachea.

In one embodiment, a portion of an organ or tissue or ECM thereof, is employed in the methods of the invention, e.g., an atrium or ventricle of a heart or interior structure of a pancreas including islets. In one embodiment, the portion is about 5 to about 10 mm in thickness. In one embodiment, the portion is about 70 to about 100 mm in thickness.

The ECM of an organ or tissue, or a vascularized portion thereof, may be obtained from any source including, without limitation, heart, liver, lungs, skeletal muscles, brain, pancreas, spleen, kidneys, uterus, eye, spinal cord, intestine, omentum, whole muscle, or bladder, or any portion thereof (e.g., an aortic valve, a mitral valve, a pulmonary valve, a tricuspid valve, a pulmonary vein, a pulmonary artery, coronary vasculature, septum, a right atrium, a left atrium, a right ventricle, or a left ventricle). A solid organ refers to an organ that has a "substantially closed" vasculature system. A "substantially closed" vasculature system with respect to an organ means that, upon perfusion with a liquid, the majority of the liquid is contained within the solid organ or pass out the native vascular structures and does not leak out of the solid organ, assuming the major vessels are cannulated, ligated, or otherwise restricted. Despite having a "substantially closed" vasculature system, many of the organs listed above have defined "entrance" and "exit" vessels which are useful for introducing and moving the liquid throughout the organ during perfusion. In addition, other types of vascularized organs or tissues such as, for example, all or portions of joints (e.g., knees, shoulders, or hips), anus, trachea, or spinal cord, can be perfusion decellularized. Further, avascular tissues such as, for example, cartilage or cornea, may be decellularized when part of a larger vascularized structures such as a whole leg.

Perfusion decellularized matrices of organs with a substantially closed vascular system are useful because perfusion decellularization preserves the intact matrix and microenvironment, including an intact vascular and microvascular system, that vascular system, or ducts or other conduits, may be utilized to deliver cells as well as nutrients and/or differentiation or maintenance factors, to the cells in vitro. Cells and nutrients and/or other factors may be delivered by other means, e.g., injection, or passive means, or a combination thereof. In one embodiment, a cell population of interest is perfused into the perfusion decellularized organ ECM after inflation allowing for the seeding into the interstitial space or matrix outside of the vascular conduits. This includes the active migration and/or homing of cells to their native microstructure, e.g. the homing of endothelial cells to the vasculature. In one embodiment, a cell population of interest is perfused into the perfusion decellularized ECM followed by a second cell population, e.g., a beta cell population is introduced followed by an endothelial cell population, where the endothelial cells remain in the vascular conduits as in their native microenvironment. In one embodiment, a cell population of interest is perfused into the perfusion decellularized ECM after inflation followed by a second cell population, e.g., an endothelial cell population is introduced followed by a population of cells that include beta cells, where the endothelial cells remain in the vascular conduits as in their native microenvironment. In another embodiment, two or more cell populations are combined and perfused together. In another embodiment, two or more distinct cell populations are introduced serially through either perfusion, direct injection or a combination of both.

The cells may be introduced in media that support the proliferation, metabolism, and/or differentiation of the cells. Alternatively, after the cells have populated the ECM, the medium is changed to one that supports the proliferation, metabolism and differentiation of the cells. The cultured cells may exist in the ECM at physiological cell densities and, in the presence of media that support the proliferation, metabolism, and/or differentiation of the cells and/or the appropriate microenvironment in the ECM, allow for the maintenance and/or functional differentiation of the cells.

The cells and ECM may be xenogeneic or allogeneic. In one embodiment, partially or completely differentiated human cells and a perfusion decellularized organ or tissue from a small animal, e.g., a nonhuman mammal, can be combined. In one example, a perfusion decellularized liver matrix from a human is seeded with endothelial cells and partially differentiated human ES derived hepatocyte cells providing allogeneic or xenogeneic, respectively, cell seeded matrices.

Decellularization of Organs or Tissues

Decellularization generally includes the following steps: stabilization of the solid organ, e.g., a vascularized structure thereof, or tissue, decellularization of the solid organ or tissue, renaturation and/or neutralization of the solid organ or tissue, washing the solid organ, degradation of any DNA remaining on the organ, disinfection of the organ or tissue and homeostasis of the organ.

The initial step in decellularizing an organ vascularized structure or tissue is to cannulate the organ or tissue. The vessels, ducts, and/or cavities of an organ or tissue may be cannulated using methods and materials known in the art. Next, the cannulated organ vascularized structure or tissue is perfused with a cellular disruption medium. Perfusion through an organ can be multi-directional (e.g., antegrade and retrograde).

Langendorff perfusion of a heart is routine in the art, as is physiological perfusion (also known as four chamber working mode perfusion). See, for example, Dehnert, The Isolated Perfused Warm-Blooded Heart According to Langendorff, In Methods in Experimental Physiology and Pharmacology: Biological Measurement Techniques V. Biomesstechnik-Verlag March GmbH, West Germany, 1988.

Briefly, for Langendorff perfusion, the aorta is cannulated and attached to a reservoir containing physiological solution to allow the heart to function outside of the body for a specified duration of time. To achieve perfusion decellularization the protocol has been modified to perfuse a cellular disruption medium delivered in a retrograde direction down the aorta either at a constant flow rate delivered, for example, by an infusion or roller pump or by a constant hydrostatic pressure pump. In both instances, the aortic valves are forced shut and the perfusion fluid is directed into the coronary ostia (thereby perfusing, via antegrade, the entire ventricular mass of the heart), which then drains into the right atrium via the coronary sinus. For working mode perfusion, a second cannula is connected to the left atrium and perfusion can be changed to retrograde.

In one embodiment, a physiological solution includes phosphate buffer saline (PBS). In one embodiment, the physiological solution is a physiologically compatible buffer supplemented with, e.g., nutritional supplements (for instance, glucose). For liver, the physiological solution may be Krebs-Henseleit buffer having 118 mM NaCl, 4.7 mM KCl, 1.2 mM $MgSO_4$, 1.2 mM $KH_2PO_4$, 26 mM $NaHCO_3$, 8 mM glucose, and 1.25 mM $CaCl_2$ supplemented with 2% BSA. For re-endothelialized liver grafts with islet, beta-cells or insulin like cells, the physiological solution may be Miami modified media-1 supplemented with or without prolactin or modified CMRL 1066 tissue culture media containing: 10% fetal bovine serum, 25 mM HEPES, 100 units/ml penicillin, and 100 µg/ml streptomycin, pH 7.4 with or without VEGF.

Methods are known in the art for perfusing other organ or tissues. By way of example, the following references describe the perfusion of lung, liver, kidney, brain, and limbs. Van Putte et al., *Ann. Thorac. Surg.*, 74(3):893 (2002); den Butter et al., *Transpl. Int.*, 8:466 (1995); Firth et al., *Clin. Sci.* (*Lond.*), 77(6):657 (1989); Mazzetti et al., *Brain Res.*, 999(1):81 (2004); Wagner et al., *J. Artif. Organs*, 6(3):183 (2003).

One or more cellular disruption media may be used to decellularize an organ or tissue. A cellular disruption medium generally includes at least one detergent such as but not limited to SDS, PEG, CHAPS or Triton X. A cellular disruption medium can include water such that the medium is osmotically incompatible with the cells. Alternatively, a cellular disruption medium can include a buffer (e.g., PBS) for osmotic compatibility with the cells. Cellular disruption media also may include enzymes such as, without limitation, one or more collagenases, one or more dispases, one or more DNases, or a protease such as trypsin. In some instances, cellular disruption media also or alternatively may include inhibitors of one or more enzymes (e.g., protease inhibitors, nuclease inhibitors, and/or collegenase inhibitors).

In certain embodiments, a cannulated organ or tissue may be perfused sequentially with two different cellular disruption media. For example, the first cellular disruption medium may include an anionic detergent such as SDS and the second cellular disruption medium can include an ionic detergent such as Triton X. Following perfusion with at least one cellular disruption medium, a cannulated organ or tissue may be perfused, for example, with wash solutions and/or solutions containing one or more enzymes such as those disclosed herein.

Alternating the direction of perfusion (e.g., antegrade and retrograde) may assist in decellularizing the entire organ or tissue. Decellularization generally decellularizes the organ from the inside out, resulting in very little damage to the ECM. An organ or tissue may be decellularized at a suitable temperature between 4 and 40° C. Depending upon the size and weight of an organ or tissue and the particular detergent(s) and concentration of detergent(s) in the cellular disruption medium, an organ or tissue generally is perfused from about 0.05 hours to about 5 hours, per gram of solid organ or tissue (generally >50 grams), or about 2 hours to about 12 hours, per gram of solid organ or tissue for organs (generally <50 grams), with cellular disruption medium. Including washes, an organ may be perfused for up to about 0.75 hours to about 10 hours per gram of solid organ or tissue (generally >50 grams), or about 12 hours to about 72 hours, per gram of tissue (generally <50 grams). Decellularization time is dependent upon the vascular and cellular density of the organ or tissue with limited scaling for overall mass. Therefore, as general guidance the time ranges and masses above are provided. Perfusion generally is adjusted to physiologic conditions including pulsatile flow, rate and pressure.

A decellularized organ or tissue has the extracellular matrix (ECM) component of all or most regions of the organ or tissue, including ECM components of the vascular tree. ECM components can include any or all of the following: fibronectin, fibrillin, laminin, elastin, members of the collagen family (e.g., collagen I, III, and IV), ECM associated growth proteins including growth factors and cytokines, glycosaminoglycans, ground substance, reticular fibers and thrombospondin, which can remain organized as defined structures such as the basal lamina. Successful decellularization is defined as the absence of detectable myofilaments, endothelial cells, smooth muscle cells, and nuclei in histologic sections using standard histological staining procedures or removal of over 97% of detectable DNA as measured by fluorometric assay. Residual cell debris may be removed from the decellularized organ or tissue.

The morphology and the architecture of the ECM is maintained during and following the process of decellularization. "Morphology" as used herein refers to the overall shape of the organ, tissue or of the ECM, while "architecture" as used herein refers to the exterior surface, the interior surface, and the ECM therebetween.

The morphology and architecture of the ECM may be examined visually and/or histologically. For example, the basal lamina on the exterior surface of a solid organ or within the vasculature of an organ or tissue should not be removed or significantly damaged due to perfusion decellularization. In addition, the fibrils of the ECM should be similar to or significantly unchanged from that of an organ or tissue that has not been decellularized.

One or more compounds may be applied in or on a decellularized organ or tissue to, for example, preserve the decellularized organ, or to prepare the decellularized organ or tissue for recellularization and/or to assist or stimulate cells during the recellularization process. Such compounds include, but are not limited to, one or more growth factors (e.g., VEGF, DKK-1, FGF, BMP-1, BMP-4, SDF-1, IGF, HGF, Activin A, Retinoic Acid, and bFGF), immune modulating agents (e.g., cytokines, glucocorticoids, IL2R antagonist, leucotriene antagonists), chemical (clozapine-N-oxide, phosphoinositide-3-kinase inhibitor, and Nicotinamide) and/or factors that modify the coagulation cascade (e.g., aspirin, heparin-binding proteins, and heparin). In addition, a decellularized organ or tissue may be further treated with, for example, irradiation (e.g., UV, gamma) to reduce or eliminate the presence of any type of microorganism remaining on or in a decellularized organ or tissue.

Exemplary Perfusion Decellularization of Heart
PEG Decellularization Protocol

Hearts are washed in 200 ml PBS containing 100 U/mL penicillin, 0.1 mg/mL Streptomycin, 0.25 µg/mL Amphotericin B, 1000 U of hepatin, and 2 mg of Adenocard with no recirculation. Hearts are then decellularized with 35 ml polyethyleneglycol (PEG, 1 g/mL) for up to 30 minutes with manual recirculation. The organ is then washed with 500 mL PBS for up to 24 hours using a pump for recirculation. The washing step is repeated at least twice for at least 24 hours each time. Hearts are exposed to 35 ml DNase I (70 U/mL) for at least 1 hour with manual recirculation. The organs are washed again with 500 ml PBS for at least 24 hours.

Triton X and Trypsin Decellularization Protocol

Hearts are washed in 200 ml PBS containing 100 U/mL Penicillin, 0.1 mg/mL Streptomycin, 0.25 µg/mL Amphotericin B, 1000 U of hepatin, and 2 mg of Adenocard for at least about 20 minutes with no recirculation. Hearts are then decellularized with 0.05% Trypsin for 30 minutes followed by perfusion with 500 mL PBS containing 5% Triton-X and 0.1% ammonium-hydroxide for about 6 hours. Hearts are perfused with deionized water for about 1 hour, and then perfused with PBS for 12 hours. Hearts are then washed 3 times for 24 hours each time in 500 mL PBS using a pump for recirculation. The hearts are perfused with 35 ml DNase I (70 U/mL) for 1 hour with manual recirculation and washed twice in 500 mL PBS for at least about 24 hours each time using a pump for recirculation.

1% SDS Decellularization Protocol

Hearts are washed in 200 mL PBS containing 100 U/mL Penicillin, 0.1 mg/mL Streptomycin, 0.25 µg/mL Amphotericin B, 1000 U of hepatin, and 2 mg of Adenocard for at least about 20 minutes with no recirculation. The hearts are decellularized with 500 mL water containing 1% SDS for at least about 6 hours using a pump for recirculation. The hearts are then washed with deionized water for about 1 hour and washed with PBS for about 12 hours. The hearts are washed three times with 500 mL PBS for at least about 24 hours each time using a pump for recirculation. The heart is then perfused with 35 ml DNase I (70 U/mL) for about 1 hour using manual recirculation, and washed three times with 500 mL PBS for at least about 24 hours each time using a pump for recirculation.

Triton X Decellularization Protocol

Hearts are washed with 200 mL PBS containing 100 U/mL Penicillin, 0.1 mg/ml Streptomycin, 0.25 g/mL Amphotericin B, 1000 U of hepatin, and 2 mg of Adenocard (adenosine) for at least about 20 minutes with no recirculation. Hearts are then decellularized with 500 mL water containing 5% Triton X and 0.1% ammonium hydroxide for at least 6 hours using a pump for recirculation. Hearts are then perfused with deionized water for about 1 hour and then with PBS for about 12 hours. Hearts are washed by perfusing with 500 mL PBS 3 times for at least 24 hours each time using a pump for recirculation. Hearts are then perfused with 35 ml DNase 1 (70 U/mL) for about 1 hour using manual recirculation, and washed three times in 500 ml PBS for about 24 hours each time.

Hearts may be perfused at a coronary perfusion pressure of 60 cm $H_2O$. Although not required, the hearts may be mounted in a decellularization chamber and completely submerged and perfused with PBS containing antibiotics for 72 hours in recirculation mode at a continuous flow of 5 mL/minute to wash out as many cellular components and detergent as possible.

Detection of Decellularization

Successful decellularization may be measured by the lack of nucleic acid in histologic sections. Successful preservation of vascular structures may be assessed by perfusion with 2% Evans Blue prior to embedding tissue sections. Highly efficient decellularization may be observed when an organ is first perfused antegradely with an ionic detergent (1% sodium-dodecyl-sulfate (SDS), approximately 0.03 M)

dissolved in deionized $H_2O$ at a constant coronary perfusion pressure and then perfused antegradely with a non-ionic detergent (1% Triton X-100) to remove the SDS and presumably to renature the extracellular matrix (ECM) proteins. Intermittently, the organ may be perfused retrogradely with phosphate buffered solution to clear obstructed capillaries and small vessels.

To demonstrate intact vascular structures following decellularization, a decellularized organ may be stained via Langendorff perfusion with Evans Blue to stain vascular basement membrane and quantify macro- and micro-vascular density.

Recellularization of Inflated Organs or Tissues

An inflated decellularized organ or tissue is contacted with a population of cells, either differentiated (mature or primary) cells, stem cells, or partially differentiated cells. Thus, the cells can be totipotent cells, pluripotent cells, or multipotent cells, and can be uncommitted or committed, and may be single-lineage cells. The cells may be undifferentiated cells, partially differentiated cells, or fully differentiated cells including fetal derived cells. Cells may include progenitor cells, precursor cells, or "adult" derived stem cells including umbilical cord cells and fetal stem cells. Cells useful in the matrices of the invention include embryonic stem cells (as defined by the National Institute of Health (NIH); see, for example, the Glossary at stemcells.nih.gov on the World Wide Web) and iPS cells.

Examples of cells that can be used to recellularize an inflated decellularized organ or tissue include, without limitation, embryonic stem cells, umbilical cord blood cells, tissue-derived stem or progenitor cells, bone marrow-derived step or progenitor cells, blood-derived stem or progenitor cells, mesenchymal stem cells (MSC), skeletal muscle-derived cells, multipotent adult progenitor cells (MAPC), or iPS cells Additional cells that can be used include cardiac stem cells (CSC), multipotent adult cardiac-derived stem cells, cardiac fibroblasts, cardiac microvasculature endothelial cells, aortic endothelial cells, coronary endothelial cells, microvascular endothelial cells, venous endothelial cells, arterial endothelial cells, smooth muscle cells, cardiomyocytes, hepatocytes, beta-cells, keratinocytes, purkinji fibers, neurons, bile duct epithelial call, islet cells, pneumocytes, clara cells, brush boarder cells, or podocytes. Bone marrow-derived stem cells such as bone marrow mononuclear cells (BM-MNC), endothelial or vascular stem or progenitor cells, and peripheral blood-derived stem cells such as endothelial progenitor cells (EPC) may also be used as cells.

The number of cells that are introduced into and onto a perfusion decellularized inflated scaffold may depend both the organ (e.g., which organ, the size and weight of the organ) or tissue and the type and developmental stage of the regenerative cells. Different types of cells may have different tendencies as to the population density those cells will reach. Similarly, different organ or tissues may be cellularized at different densities. By way of example, an inflated decellularized organ or tissue can be "seeded" with at least about 1,000 (e.g., at least 10,000, 100,000, 1,000,000, 10,000,000, or 100,000,000) cells; or can have from about 1,000 cells/mg tissue (wet weight, e.g., prior to decellularization) to about 10,000,000 cells/mg tissue (wet weight) attached thereto.

Cells can be introduced ("seeded") into an inflated decellularized organ or tissue by injection into one or more locations. In addition, more than one type of cell may be introduced into an inflated decellularized organ or tissue. For example, a population of differentiated cell types can be injected at multiple positions in an inflated decellularized organ or tissue or different cell types may be injected into different portions of a decellularized organ or tissue. Alternatively, or in addition to injection, cells or a cocktail of cells may be introduced by perfusion into a cannulated inflated decellularized organ or tissue. For example, cells can be perfused into an inflated decellularized organ using a perfusion medium, which can then be changed to an expansion and/or differentiation medium to induce growth and/or differentiation of the cells. Location specific differentiation may be achieved by placing cells into the various locations within the organ, e.g., into regions of the heart, such as, atrial, ventricular or nodal.

During recellularization, an organ or tissue is maintained under conditions in which at least some of the cells can multiply and/or differentiate within and on the decellularized organ or tissue. Those conditions include, without limitation, the appropriate temperature and/or pressure, electrical and/or mechanical activity, force, the appropriate amounts of $O_2$ and/or $CO_2$, an appropriate amount of humidity, and sterile or near-sterile conditions. During recellularization, the decellularized organ or tissue and the regenerative cells attached thereto are maintained in a suitable environment. For example, the cells may require a nutritional supplement (e.g., nutrients and/or a carbon source such as glucose), exogenous hormones or growth factors, and/or a particular pH.

The methods of recellularizing a tissue or organ matrix as described herein include perfusing a tissue or organ matrix with a physiological buffer under pressure. This perfusion of the tissue or organ matrix under pressure is performed prior to introducing any cells into the matrix and, similar to the perfusion used in the decellularization process described in WO 2007/025233, is via the vasculature or other lumen or conduit structure (e.g., the trachea in lungs, the bile duct in liver, the urethra in kidney, etc.) of the organ or tissue matrix, and generally begins with cannulation of the vasculature (e.g., arteries, veins, arterioles, venules and capillaries) and/or other lumens and/or conduits (referred to hereinafter as "vasculature-type" structures) of an organ or tissue matrix (about 1 to about 300 Hg). Cannulation thus includes the insertion of a cannula into a body duct, cavity or vessel, as into the trachea, bladder, or a blood vessel to introduce or remove a fluid, substance or waste. As used herein, perfusion of an organ or tissue matrix under pressure refers to delivering a fluid composition (e.g., a physiological buffer) under enough pressure such that the vasculature and vasculature-type structures in the tissue or organ matrix remains open and expanded, but not so high as to cause damage or distension to the vasculature or vasculature-type structures of the tissue or organ matrix. A physiological buffer suitable for pre-cellular perfusion of a tissue or organ matrix under pressure can be any buffer that is compatible with the tissue or organ matrix. For example, physiological buffers can include nutrients such as sugars and carbohydrates, and also can include pro-endothelial factors (e.g., compounds that have a positive effect on endothelial cells or endothelium) such as, for example, compounds that induce angiogenesis (e.g., VEGF, FGF-1 and/or bFGF). A physiological buffer is generally at physiological pH.

In one embodiment, the physiological buffer suitable for pre-cellular perfusion or cellular perfusion includes but is not limited to phosphate buffer saline (PBS) or culture media solutions suitable for endothelial cell culture including but not limited to EGM-2, EGM-2MV, DMEM, PromoCell Endothelial Cell Medium, Medium 200, DMEMF/12, buffers along with nutritional supplements, e.g., glucose, that may be employed for organ perfusion and/or preservation including transplantation. Those include, for example for heart tissues, Modified Krebs-Henseleit buffer of the following composition was prepared (in mM): 118 NaCl, 4.7 KCl, 1.2 MgSO$_4$, 1.2 KH$_2$PO$_4$, 25 NaHCO$_3$, 11 glucose, 1.75 CaCl$_2$, and 2.0 pyruvate and 5 U/L insulin or Krebs buffer containing (in mM) 118 NaCl, 4.7 KCl, 25 NaHCO$_3$, 1.2 MgSO$_4$, 1.2 $_{KH2PO4}$, 2 CaCl$_2$ gassed with 95% O2, 5% CO2; or glucose (e.g., 11 mM) or glucose in combination with 1 or 1.2 mM palmitate. For kidney tissues, an exemplary medium is KPS-1 Kidney Perfusion Solution. For liver tissues, an exemplary medium is Krebs-Henseleit buffer containing 118 mM NaCl, 4.7 mM KCl, 1.2 mM MgSO$_4$, 1.2 mM KH$_2$PO$_4$, 26 mM NaHCO$_3$, 8 mM glucose, and 1.25 mM CaCl$_2$ supplemented with 2% BSA.

Although not bound by any particular mechanism, it is thought that this pre-cellular perfusion under pressure opens and flushes out the matrix and, particularly, the vascular bed of the tissue or organ matrix, thereby exposing more of the matrix to the cells during re-endothelialization and allowing the establishment of a viable endothelium throughout the vasculature of the tissue or organ matrix. It would be understood by those skilled in the art that different tissues and organ matrices (e.g., from different sources, e.g., a heart, liver, lung, kidney, pancreas, etc.) can withstand different amounts of pressure. The amount of pressure a particular tissue or organ matrix can withstand is related, at least in part, to the vascular bed of that particular tissue or organ matrix.

Cells may be allogeneic to a decellularized organ or tissue (e.g., a human decellularized organ or tissue seeded with human cells), or cells may be xenogeneic to a decellularized organ or tissue (e.g., a pig decellularized organ or tissue seeded with human cells). "Allogeneic" as used herein refers to cells obtained from the same species as that from which the organ or tissue originated (e.g., related or unrelated individuals), while "xenogeneic" as used herein refers to cells obtained from a species different than that from which the organ or tissue originated.

Stem or progenitor media may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR or hLIF (human leukemia inhibitory factor). The cell differentiation media may also contain supplements such as L-Glutamine, NEAA (non-essential amino acids), P/S (penicillin/streptomycin), N2, B27 and beta-mercaptoethanol. It is contemplated that additional factors may be added to the cell differentiation media, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, high dose activin, and amnionless or variants or functional fragments thereof. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be added to promote mesendoderm stem/progenitor, endoderm stem/progenitor, mesoderm stem/progenitor, or definitive endoderm stem/progenitor proliferation and survival as well as survival and differentiation of derivatives of these progenitors.

In one embodiment, inflated decellularized matrices are combined with iPS or ES cells differentiated using the embryoid body (EB) method. For example, human iPS cell lines reprogrammed by transduction, e.g., lentiviral-mediated transduction, of transcription factors (OCT4, SOX2, NANOG and LIN28; Oct3/4, Sox2, Klf4, and c-Myc; or Oct3/4, Sox2, and Klf4) are employed. iPS clones of fetal origin or of newborn origin may be employed. Human ES cell lines may also be employed. iPS cells and ES cells may be maintained on irradiated mouse embryonic fibroblasts (MEFs) at a density of 19,500 cells/cm$^2$ in 6-well culture plates (Nunc) in DMEM/F12 culture medium supplemented with 20% KnockOut serum replacer (Invitrogen), 0.1 mmol/L nonessential amino acids, 1 mmol/L L-glutamine, and 0.1 mmol/L β-mercaptoethanol (Sigma). In addition, the medium may be supplemented with 100 ng/mL, zebrafish basic fibroblast growth factor for iPS cells, and with 4 ng/mL human recombinant basic fibroblast growth factor (Invitrogen) for hES cells. iPS and ES cell lines may also be maintained on gelatinized 100-mm dishes in DMEM (Sigma-Aldrich) containing 15% fetal calf serum (FCS; Sigma-Aldrich), 0.1 μmol/L 2-mercaptoethanol (2ME), and 1,000 units/ml LIF (Chemicon International). For differentiation, these cells may treated with 0.25% Trypsin/ethylenediaminetetraacetic acid (GIBCO), and transferred to gelatinized 6-well plates in α-minimum essential medium (GIBCO) supplemented with 10% FCS and 0.05 μmol/L 2ME, at a concentration of 3×10$^4$ cells/well.

Colonies may be detached from culture plates by incubating with 1 mg/mL dispase (Gibco) solution at 37° C. for 8 to 15 minutes and placed in ultralow attachment plates in suspension culture, e.g., for 4 days. During suspension culture, the medium may be changed at day 1 followed by culture for another 3 days without medium change. EBs are then plated on 0.1% gelatin-coated culture plates, e.g., at the density or 50 to 100 EBs per well, or in the perfusion decellularized ECM and cultured in differentiation medium (e.g., changed daily).

In some instances, an organ or tissue generated by the methods described herein is to be transplanted into a patient. In those cases, the cells used to recellularize a decellularized organ or tissue can be obtained from the patient such that the cells are "autologous" to the patient. Cells from a patient can be obtained from, for example, blood, bone marrow, tissues, or organs at different stages of life (e.g., prenatally, neonatally or perinatally, during adolescence, or as an adult) using methods known in the art. Alternatively, cells used to recellularize a decellularized organ or tissue may be syngeneic (i.e., from an identical twin) to the patient, cells can be human lymphocyte antigen (HLA)-matched cells from, for example, a relative of the patient or an HLA-matched individual unrelated to the patient, or cells can be allogeneic to the patient from, for example, a non-HLA-matched donor.

Irrespective of the source of the cells (e.g., autologous or not), the decellularized solid organ can be autologous, allogeneic or xenogeneic to a patient.

The progress of cells can be monitored during recellularization. For example, the number of cells on or in an organ or tissue can be evaluated by taking a biopsy at one or more time points during recellularization. In addition, the amount of differentiation that cells have undergone can be monitored by determining whether or not various markers are present in a cell or a population of cells. Markers associated with different cells types and different stages of differentiation for those cell types are known in the art, and can be readily detected using antibodies and standard immunoassays. See, for example, Current Protocols in Immunology, 2005, Coligan et al., Eds., John Wiley & Sons, Chapters 3 and 11. Nucleic acid assays as well as morphological and/or histological evaluation can be used to monitor recellularization.

Endothelial progenitor cells (EPCs) are immature endothelial cells, which have the capacity to proliferate, migrate, and differentiate into endothelial cells but have not yet acquired characteristics of mature endothelial cells. EPCs may be mobilized from bone marrow into peripheral blood (circulating EPCs) in response to certain physiological stimuli, such as, for example, tissue injury. Circulating EPCs were identified in adult human blood (Asahara et al. (1997) Science 275:964-967) and subsequent studies have suggested a role for EPCs in the maintenance of endothelial integrity and function, as well as in postnatal neovascularization. EPCs can be isolated from blood, bone marrow, or cord blood and are identified in the CD34+ cell fraction in adult human peripheral mononuclear cells. These can be isolated using CD34+ cells or CD133+ cells alone or in combination with KDR+ as an EPC-rich cell fraction in peripheral blood via direct FACS sorting or other available ex-vivo selection method such as magnetic beads, microfluidics, lab-on-a-chip, affinity column or associated device. EPCs can then either be directly perfused onto the matrix and cultured under appropriate conditions to assist with proliferation and differentiation, or cultured in-vitro to increase overall cell numbers in an EPC maintaining culture medium such as culturing for seven days in serum free StemSpan® medium (StemCell Technologies, Vancouver, Canada) during the initial expansion period and supplemented with 1% penicillin-streptomycin (Sigma-Aldrich, St. Louis, USA) and recombinant human (rh) Flt-3 ligand (100 ng/mL), rh stem cell factor (100 ng/mL), rh IL-3 (20 ng/mL), rh IL-6 (20 ng/mL). These cells and then be perfused into the matrix as EPCs or predifferentiated into ECs and perfused into the matrix. Differentiation of EPCs can be achieved through methods such as culturing about $3 \times 10^5$ to about $1 \times 10^6/1.5$ mL/9.6 cm$^2$ in endothelial cell growth medium-2 (EGM-2) containing FBS (2%), hydrocortisone, hFGF, VEGF, R$^3$-IGF-1, ascorbic acid, hEGF, gentamycin, amphotericin-B and heparin (Lonza, Basel, Switzerland). After three days of culture, the cells can be collected and transferred to plates coated with fibronectin (10 μg/ml) (Sigma-Aldrich, St. Louis, USA) at a density of about $1 \times 10^6$ cells/1.5 mL/9.6 cm$^2$ and cultured for an additional three days in fresh EGM-2 medium.

A population of allogeneic endothelial or endothelial cell precursors may be used and prepared from tissue that is allogeneic to that of the recipient and is tested for use by the well-known methods of tissue typing, to closely match the histocompatibility type of the recipient. These include but are not limited to human umbilical vein endothelial cells (HUVECs), genetically modified endothelial cells to reduce immunogenicity, HLA matched endothelial cells, cord blood derived endothelial cells. ECs derived from EPCs, progenitor, iPS or embryonic stem cells. Most allogeneic approaches will require the use of immunosuppression agents post transplantation. Recent studies have demonstrated the immune privileged nature of ECs derived from EPCs (Cardiovasc Res. 2010 Oct. 1; 88(1):121-9. Epub 2010 Apr. 13) where immune suppression would not be required post transplantation. Examples of EPC differentiation methods include: isolating EPC from the blood by density gradient centrifugation with Pancoll rat (PAN-Biotech), and performing a CD45-depletion using an CD45 monoclonal antibody. The CD45 (−) fraction is cultured in endothelial differentiation medium [EBM supplemented with 5% FCS, 50 mg/mL gentamicin, 10 ng/mL rat VEGF, 1 ng/mL bovine bFGF, 10 ng/mL murine IGF-1 (both R&D Systems), 10 ng/mL murine EGF, and 1 mg/mL hydrocortisone] in 20 mg/mL fibronectin coated dishes. Non-adherent cells were removed by medium change every 4 days. Outgrowing cell clusters appeared after about 15 to about 22 days of culture, and are picked by trypsinization inside cloning rings. PECAM-1(+) cells are selected with MACS separation using a PECAM-1 antibody and IgG1 MicroBeads. The PECAM-1(+) fraction can be further cultured up to passage 25 and can be perfused in multiple matrices.

Additionally, an alternative to employing immunosuppression techniques, methods of gene replacement or knockout using homologous recombination in stem cells, taught by Smithies et al., 317 Nature 230-234 (1985), and extended to gene replacement or knockout in cell lines (Zheng et al., 88 Proc. Natl. Acad. Sci. 8067-8071 (1991)), can be applied to endothelial and endothelial deriving cells for the ablation of major histocompatibility complex (MHC) genes. Cells lacking MHC expression allows for the grafting of enriched endothelial cell populations across allogeneic, and perhaps even xenogeneic, histocompatibility barriers without the need to immunosuppress the recipient. General reviews and citations for the use of recombinant methods to reduce antigenicity of donor cells are also disclosed by Gruber, 54 Transplantation 1-11 (1992). Exemplary approaches to the reduction of immunogenicity of transplants by surface modification are disclosed by PCT International patent application WO 92/04033 and PCT/US99/24630. Alternatively the immunogenicity of the graft may be reduced by preparing cells from a transgenic animal that has altered or deleted MHC antigens.

Endothelial cell precursors include but are not limited to colony forming unit-endothelial cells (CFU-ECs), circulating angiogenic cells (CACs), circulating endothelial precursors (CEPs), endothelial colony-forming cells (ECFC), low proliferative potential ECFC (LPP-ECFC), and high proliferative ECFC (HPP-ECFC).

In one embodiment, endothelial cells and endothelial progenitor cells are obtained by culturing embryonic stem cells (ESCs) or induced pluripotent stem cells (iPSCs) under appropriate conditions to direct the stem cells down an endothelial lineage. Endothelial progenitor cells are cells that have begun to differentiate into endothelial cells (e.g., e.g., lineage-restricted; e.g., cells that are destined to become endothelial cells) but are not considered fully differentiated endothelial cells. For example, endothelial progenitor cells can express a progenitor marker such as CD133 and also can express endothelial cell marker such as, without limitation, platelet endothelial cell-adhesion molecule-1 (PECAM1; aka CD31), VEGFR-1 (aka Fit-1), VEGFR-2 (aka Flk-1), guanylate-binding protein-1 (GBP-1), thrombomodulin (aka CD141), VE-cadherin (aka CD144), von Willebrand factor (vWF), and intercellular adhesion molecule 2 (ICAM-2). Generally, endothelial progenitor cells also are able to take up acetylated LDL, and, further, may migrate toward VEGF and/or form tubes on Matrigel.

ESCs or iPSCs, such as human ESCs and human iPSCs, can be further cultured under conditions that result in fully differentiated endothelial cells, e.g., VEGF and bFGF. Additionally or alternatively, endothelial cells can be obtained from any number of sources such as bone marrow, blood, skin, liver, heart, lung, retina, and any other tissue or organ that harbors endothelial cells. For example, representative endothelial cells include, without limitation, blood endothelial cells, bone marrow endothelial cells, circulating endothelial cells, human aorta endothelial cells, human brain microvascular endothelial cells, human dermal microvascular endothelial cells, human intestinal microvascular endothelial cells, human lung microvascular endothelial cells, human microvascular endothelial cells, hepatic sinusoidal endothelial cells, human saphenous vein endothelial cells, human umbilical vein endothelial cells, lymphatic endothelial cells, microvessel endothelial cells, microvascular endothelial cells, pulmonary artery endothelial cells, retinal capillary endothelial cells, retinal microvascular endothelial cells, vascular endothelial cells, umbilical cord blood endothelial cells, and combinations thereof. As those of skill in the art would understand, this is not intended to be an exhaustive list of endothelial cells.

EPCs may be obtained from peripheral blood by isolating peripheral blood mononuclear cells (PBMC) by density gradient centrifugation. Cell suspensions are seeded in any receptacle capable of sustaining cells, particularly culture flasks, culture plates or roller bottles, and more particularly in small culture flasks such as 25 cm$^2$ culture flasks. Cells cultured in suspension may be resuspended at approximately $5 \times 10^4$ to about $2 \times 10^5$ cells/mL (for example, about $1 \times 10^5$ cells/mL). Cells plated on a fixed substrate may be plated at approximately 2 to about $3 \times 10^3$ cells/cm$^2$. Optionally, the culture plates are coated with a matrix protein such as collagen. The cells may be placed into any known culture medium capable of supporting cell growth, including HEM, DMEM, RPMI, F-12, and the like, containing supplements which are required for cellular metabolism such as glutamine and other amino acids, vitamins, minerals and proteins such as transferrin and the like. The culture medium may also contain antibiotics to prevent contamination with yeast, bacteria and fungi such as penicillin, streptomycin, gentamicin and the like. The culture medium may contain serum derived from bovine, equine, chicken and the like. Conditions for culturing generally should be close to physiological conditions. The pH of the culture medium should be close to physiological pH. (for example, between pH 6-8, between about pH 7 to 7.8, or at pH 7.4). Physiological temperatures range between about 30° C. to 40° C. EPCs may be cultured at temperatures between about 32° C. to about 38° C. (for example, between about 35° C. to about 37° C.).

Optionally, the culture medium is supplemented with at least one proliferation-inducing ("mitogenic") growth factor. A "growth factor" is protein, peptide or other molecule having a growth, proliferation-inducing, differentiation inducing, or trophic effect on EPCs. "Proliferation-inducing growth factors" are trophic factor that allows EPCs to proliferate, including any molecule that binds to a receptor on the surface of the cell to exert a trophic, or growth-inducing effect on the cell. Proliferation-inducing growth factors include EGF, amphiregulin, acidic fibroblast growth factor (aFGF or FGF-1), basic fibroblast growth factor (bFGF or FGF-2), transforming growth factor alpha (TGFα), VEGF and combinations thereof. Growth factors are usually added to the culture medium at concentrations ranging between about 1 fg/mL to 1 mg/mL. Concentrations between about 1 to 100 ng/mL are usually sufficient. Simple titration assays can easily be performed to determine the optimal concentration of a particular growth factor. The biological effects of growth and trophic factors are generally mediated through binding to cell surface receptors. The receptors for a number of these factors have been identified and antibodies and molecular probes for specific receptors are available. EPCs can be analyzed for the presence of growth factor receptors at all stages of differentiation. In many cases, the identification of a particular receptor provides guidance for the strategy to use in further differentiating the cells along specific developmental pathways with the addition of exogenous growth or trophic factors.

Generally, after about 3-10 days in vitro, the culture medium of EPCs is replenished by aspirating the medium, and adding fresh medium to the culture flask. Optionally, the aspirated medium is collected, filtered and used as a condition medium to subsequently passage EPCs. For example the 10%, 20%, 30%, 40% or more condition medium is used. The EPC cell culture can be easily passaged to reinitiate proliferation. For example, after about 3 to about 7 days in vitro, the culture flasks are shaken well and EPCs are then transferred to a 50 mL centrifuge tube and centrifuged at low speed. The medium is aspirated, the EPCs are resuspended in a small amount of culture medium, the cells are then counted and replated at the desired density to reinitiate proliferation. This procedure can be repeated weekly to result in a logarithmic increase in the number of viable cells at each passage. The procedure is continued until the desired number of EPCs is obtained.

EPCs and EPC progeny can be cryopreserved by any method known in the art until they are needed. (See, e.g., U.S. Pat. No. 5,071,741, PCT International patent applications WO93/14191, WO95/07611, WO96/27287, WO96/29862, and WO98/14058, Karlsson et al., 65 Biophysical J. 2524-2536 (1993)). The EPCs may be suspended in an isotonic solution, preferably a cell culture medium, containing a particular cryopreservant. Such cryopreservants include dimethyl sulfoxide (DMSO), glycerol and the like. These cryopreservants may be used at a concentration of 5-15% (for example, 8-10%). Cells are frozen gradually to a temperature of −10° C. to −150° C. (for example, −20° C. to −100° C., or −70° C. to −80° C.

Depending on the culture conditions, EPCs may be differentiated into endothelial cells or smooth muscle cells. EPCs can be differentiated into endothelial cells or smooth muscle cells EPCs on a fixed substrate in a culture medium with a differentiation-inducing growth factor. Differentiation of the EPCs can also be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Instead of proliferation-inducing growth factors for the proliferation of EPCs (see above), differentiation-inducing growth factors can be added to the culture medium to influence differentiation of the EPCs. Other differentiation inducing growth factors include platelet derived growth factor (PDGF), thyrotropin releasing hormone (TRH), transforming growth factor betas (TGF,s), insulin-like growth factor (IGF-1) and the like.

Differentiated endothelial cells or smooth muscle cells may be detected using immunocytochemical techniques know in the art. Immunocytochemistry (e.g. dual-label immunofluorescence and immunoperoxidase methods) uses antibodies that detect cell proteins to distinguish the cellular characteristics or phenotypic properties of endothelial cells or smooth muscle cells Cellular markers for endothelial cells include for example, VE-cadherin, CD144, CD141, CD 106, or CD142 whereas cellular markers for smooth muscle cells includes Flk. Immunocytochemistry can also be used to identify endothelial cells, by detecting the expression of endothelial cell genes such as CD31 and e-NOS.

In situ hybridization histochemistry may also be performed, using cDNA or RNA probes specific for the endothelial gene mRNAs. These techniques can be combined with immunocytochemical methods to enhance the identification of specific phenotypes. If necessary, the antibodies and molecular probes discussed above can be applied to Western and Northern blot procedures respectively to aid in cell identification.

Endothelial cells can be obtained, for example, from one of the many depositories of biological material around the world. See, for example, the American Type Culture Collection (ATCC.org on the World Wide Web) or the International Depositary Authority of Canada (IDAC; nml-lnm.gc.ca on the World Wide Web). Endothelial cells or endothelial progenitor cells also can be obtained from the individual that will be the recipient of the transplanted tissue or organ matrix. These cells would be considered to be autologous to the recipient. Additionally, under certain circumstances, the relationship between the tissue or organ matrix and the endothelial cells or endothelial progenitor cells can be allogeneic (i.e., different individuals from the same species); in other instances, the relationship between the tissue or organ matrix and the endothelial cells or endothelial progenitor cells can be xenogeneic (i.e., individuals from different species). In certain instances, the tissue or organ matrix is xenogeneic to the recipient and the endothelial or endothelial-progenitor cells are allogeneic to the recipient.

A composition that includes endothelial cells or endothelial progenitor cells typically is delivered to a tissue or organ matrix in a solution that is compatible with the cells (e.g., in a physiological composition) under physiological conditions (e.g., 37° C.). A physiological composition, as referred to herein, can include, without limitation, buffers, nutrients (e.g., sugars, carbohydrates), enzymes, expansion and/or differentiation medium, cytokines, antibodies, repressors, growth factors, salt solutions, or serum-derived proteins. As used herein, a composition that "consists essentially of" endothelial cells or endothelial progenitor cells is a composition that is substantially free of cells other than endothelial cells or endothelial progenitor cells but may still include any of the components that might be found in a physiological composition (e.g., buffers, nutrients, etc.).

To optimize re-endothelialization, endothelial cells or endothelial progenitor cells generally are introduced into an organ or tissue matrix by perfusion. As with the pre-cellular perfusion, and as described in WO 2007/025233, perfusion occurs via the vasculature or vasculature-type structure (e.g., other lumens or conduits) of the organ or tissue matrix. Perfusion to re-endothelialize an organ or tissue matrix should be at a flow rate that is sufficient to circulate the physiological composition of cells through the vasculature and vasculature-type structures; however, perfusion to re-endothelialize a tissue or organ matrix typically is performed under little to no pressure (e.g., less pressure than is used in the pre-cellular perfusion step to expand and flush the vascular bed). Perfusion with the endothelial cells or endothelial progenitor cells can be multi-directional (e.g., antegrade and retrograde) to even further optimize re-endothelialization.

The number of endothelial cells or endothelial progenitor cells that is introduced into a tissue or organ matrix for re-endothelialization is dependent on both the organ or tissue (e.g., which organ or tissue, the size and weight of the organ or tissue, the developmental stage of the organ or tissue, and/or the extent of vascularization of the organ or tissue) and the type and developmental stage of the endothelial cells, endothelial derived, immature endothelial cells, or endothelial progenitor cells. In addition, more than one type of endothelial cells or endothelial progenitor cells (e.g., a cocktail of endothelial cells or endothelial progenitor cells) can be perfused into an organ or tissue matrix. Different types of endothelial cells or endothelial progenitor cells may have different tendencies as to the population density those cells will reach, and, similarly, different organ or tissue matrices may be re-endothelialized at different densities. Simply by way of example, at least about 100 (e.g., at least about $10^3$, $10^4$, $10^5$, $10^6$, $10^7$, $10^9$ or $10^{10}$) endothelial cells or endothelial progenitor cells can be introduced into an organ or tissue matrix.

Prior to implantation the matrix or graft should contain a majority of mature endothelial cells as defined by the expression of cellular markers for endothelial cells include for example, VE-cadherin, CD144, CD141, CD 106, or CD142. Immunocytochemistry may also be used to identify endothelial cells, by detecting the expression of endothelial cell genes such as CD31 and e-NOS. A non-destructive method of endothelial isolation would be the brief perfusion of trypsin (0.25% or less) or other cell detachment method to enable the removal of a small fraction <0.01% of the endothelial cells which then can be assayed for the expression of endothelial cell markers including but not limited to CD105, CD31 and functional expression of e-NOS. In additional function of the endothelial cells may be assessed through endothelial tube formation in Matrigel assays. In brief, wells of a 96-well plate were coated with 50 µL ice cold Matrigel™ followed by incubation at 37° C. for one hour. Thereafter, 100 µL EGM-2 medium containing about 25,000 to about 50,000 endothelial cells are added to the Matrigel™. Incubation is carried out for 16 hours in a humidified atmosphere at 37° C. with 5% $CO_2$. Tube formation is assessed with an inverted microscope and digital photomicrographs of each single well were taken at a four times magnification and the total number of tubes, the branching points, the length of the tubes as well as the sum of the lengths of the tubes can be calculated for each well were the presence of endothelial tubes defined functional endothelial cells.

In addition, measurement of re-endothelialization can be completed through the use of standard hemocompatibility tests and assays including but not limited to, platelet activation, oxidative burst, hemolysis, fibrinolysis, fibrin formation, generation of thrombin, contact activation, and complement activation. Non-destructive methods include the use of proliferation assay such at CellTiter Blue or other metabolic assays to determine the density of endothelial cells present in the matrix which can be extrapolated to known values of native tissue where the goal is to have >50% endothelial cell density of a native tissue.

Measurement of re-endothelialization may be conducted through the use of standard hemocompatibility tests and assays including but not limited to, platelet activation, oxidative burst, hemolysis, fibrinolysis, fibrin formation, generation of thrombin, contact activation, and complement activation. Non-destructive methods include the use of proliferation assay such at CellTiter Blue or other metabolic assays to determine the density of endothelial cells present in the matrix which can be extrapolated to known values of native tissue where the goal is to have >50% endothelial cell density of a native tissue.

Perfusion pressures for the introduction of endothelial cells generally corresponds to the native perfusion pressures of the tissues or organs of which the matrix or scaffold had been derived within in range of +/−300% as the vasculature is capable of sustaining pressures >300 mm Hg.

A re-endothelialized tissue or organ matrix as described herein can be transplanted into a recipient. Such a re-endothelialized tissue or organ matrix exhibits very little thrombogenesis and very little immunogenicity. Such a re-endothelialized tissue or organ matrix, once transplanted, can be further recellularized in vivo. After transplantation, such a re-endothelialized tissue or organ matrix can be recellularized in vivo (i.e., with native cells from the recipient). Recellularization in vivo can include further re-endothelialization and/or recellularization with cells other than endothelial cells or endothelial progenitor cells (e.g., tissue- or organ-specific cells such as hepatocytes, bile duct epithelial cells, stem cells, progenitor cells, iPS cells, bone marrow mononuclear cells, smooth muscle cells cardiomyocytes, cardiac fibroblasts, fibroblasts, kuffner cells, skeletal muscle cells, satellite cell, kidney glomerulus parietal cell, kidney glomerulus podocyte, kidney proximal tubule brush border cell, loop of Henle thin segment cell, kidney distal tubule cell, kidney collecting duct cell, type I pneumocyte (lining air space of lung cell), pancreatic duct cell (centroacinar cell), beta cell, islet cells, cell, intercalated cell, intestinal brush border cell (with microvilli), exocrine gland striated duct cell, gall bladder epithelial cell, epididymal principal cell, interstitial kidney cells, and/or epididymal basal cells).

Optionally, a tissue or organ matrix can be recellularized in vitro with cells other than endothelial or endothelial progenitor cells before the tissue or organ matrix is re-endothelialized or after the tissue or organ matrix has been re-endothelialized. As used herein, cells "other than endothelial, endothelial derived or endothelial progenitor cells" refer to all the other types of cells that populate a particular tissue or organ. In the methods described herein, stem cells or progenitor cells (e.g., embryonic stem cells (ESC), adult stem cells, or induced pluropotent stem (iPS)) can be used to recellularize the parenchyma of a tissue or organ, or tissue- or organ-specific cells (i.e., differentiated or partially-differentiated cells) can be used to recellularize the parenchyma of a tissue or organ. With tissue- or organ-specific cells, the particular type of cell delivered typically depends on the type of tissue or organ that is ultimately being produced. For example, when recellularizing a heart, cardiocytes, smooth muscle cells, cardiac fibroblasts and/or cardiac stem cells can be introduced into or onto the tissue or organ matrix; when recellularizing a liver, hepatocytes, bile duct cells, smooth muscle cells, fibroblasts and/or hepatocyte progenitor cells can be introduced into or onto the tissue or organ matrix; when recellularizing a kidney, podocytes, glomerular cells, and/or epithelial cells can be introduced into or onto the tissue or organ matrix; when recellularizing a lung, epithelial cells, clara cells, goblet cells, alveolar type I, and/or alveolar type II cells can be introduced into or onto the tissue or organ matrix; when recellularizing a pancreas, beta-cells and/or islet cells can be introduced into or onto the tissue or organ matrix.

As with the endothelial cells or endothelial progenitor cells, cells other than the endothelial or endothelial progenitor cells can be delivered to a tissue or organ matrix in a physiological composition (e.g., with buffers, nutrients, enzymes, growth or differentiation medium), and can be delivered or introduced using any number of routes (e.g., injection (e.g., at multiple locations), perfusion, infusion, and/or topical application).

In embodiments in which the cells other than the endothelial or endothelial progenitor cells are introduced following the re-endothelialization of the tissue or organ matrix, it may be beneficial to allow the endothelial cells or endothelial progenitor cells some time to adhere to and become established within the vasculature of the tissue or organ matrix before any other cells are delivered. A sufficient time for endothelial cells or endothelial progenitor cells to adhere to the tissue or organ matrix is, for example, 30 to 180 minutes. However, the endothelial cells or endothelial progenitor cells can be allowed to adhere and become established in the tissue or organ matrix for up to, for example, 28-30 days (e.g., about 1 month).

Controlled System for Decellularizing and/or Recellularizing an Organ or Tissue

A system (e.g., a bioreactor) for decellularizing and/or recellularizing an organ or tissue generally includes at least one cannulation device for cannulating an organ or tissue, a perfusion apparatus for perfusing the organ or tissue through the cannula(s), and means (e.g., a containment system) to maintain a sterile environment for the organ or tissue. Cannulation and perfusion are well-known techniques in the art. A cannulation device generally includes size-appropriate hollow tubing for introducing into a vessel, duct, and/or cavity of an organ or tissue. Typically, one or more vessels, ducts, and/or cavities are cannulated in an organ. A perfusion apparatus can include a holding container for the liquid (e.g., a cellular disruption medium) and a mechanism for moving the liquid through the organ (e.g., a pump, air pressure, gravity) via the one or more cannulae. The sterility of an organ or tissue during decellularization and/or recellularization can be maintained using a variety of techniques known in the art such as controlling and filtering the air flow and/or perfusing with, for example, antibiotics, anti-fungals or other anti-microbials to prevent the growth of unwanted microorganisms.

A system to decellularize and recellularize organ or tissues as described herein can possess the ability to monitor certain perfusion characteristics (e.g., pressure, volume, flow pattern, temperature, gases, pH), mechanical forces (e.g., ventricular wall motion and stress), and electrical stimulation (e.g., pacing). As the coronary vascular bed changes over the course of decellularization and recellularization (e.g., vascular resistance, volume), a pressure-regulated perfusion apparatus is advantageous to avoid large fluctuations. The effectiveness of perfusion can be evaluated in the effluent and in tissue sections. Perfusion volume, flow pattern, temperature, partial $O_2$ and $CO_2$ pressures and pH can be monitored using standard methods.

Sensors can be used to monitor the system (e.g., bioreactor) and/or the organ or tissue. Sonomicromentry, micromanometry, and/or conductance measurements can be used to acquire pressure-volume or preload recruitable stroke work information relative to myocardial wall motion and performance. For example, sensors can be used to monitor the pressure of a liquid moving through a cannulated organ or tissue; the ambient temperature in the system and/or the temperature of the organ or tissue; the pH and/or the rate of flow of a liquid moving through the cannulated organ or tissue; and/or the biological activity of a recellularizing organ or tissue. In addition to having sensors for monitoring such features, a system for decellularizing and/or recellularizing an organ or tissue also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, an external pacemaker, and/or a compliance chamber. To help ensure stable conditions (e.g., temperature), the chambers, reservoirs and tubings can be water-jacketed.

A system for generating an organ or tissue may be controlled by a computer-readable storage medium in combination with a programmable processor (e.g., a computer-readable storage medium as used herein has instructions stored thereon for causing a programmable processor to perform particular steps). For example, such a storage medium, in combination with a programmable processor, may receive and process information from one or more of the sensors. Such a storage medium in conjunction with a programmable processor also can transmit information and instructions back to the bioreactor and/or the organ or tissue.

An organ or tissue undergoing recellularization may be monitored for biological activity. The biological activity can be that of the organ or tissue itself such as for cardiac tissue, electrical activity, mechanical activity, mechanical pressure, contractility, and/or wall stress of the organ or tissue. In addition, the biological activity of the cells attached to the organ or tissue may be monitored, for example, for ion transport/exchange activity, cell division, and/or cell viability. See, for example, Laboratory Textbook of Anatomy and Physiology (2001, Wood, Prentice Hall) and Current Protocols in Cell Biology (2001, Bonifacino et al., Eds, John Wiley & Sons). As discussed above, it may be useful to simulate an active load on an organ during recellularization. A computer-readable storage medium of the invention, in combination with a programmable processor, may be used to coordinate the components necessary to monitor and maintain an active load on an organ or tissue.

In one embodiment, the weight of an organ or tissue may be entered into a computer-readable storage medium as described herein, which, in combination with a programmable processor, can calculate exposure times and perfusion pressures for that particular organ or tissue. Such a storage medium may record preload and afterload (the pressure before and after perfusion, respectively) and the rate of flow. In this embodiment, for example, a computer-readable storage medium in combination with a programmable processor can adjust the perfusion pressure, the direction of perfusion, and/or the type of perfusion solution via one or more pumps and/or valve controls.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An inflated decellularized extracellular matrix of a mammalian organ or a vascularized portion thereof, or of a vascularized mammalian tissue or vascularized portion thereof, wherein said decellularized extracellular matrix comprises a vascular tree, duct or cavity, and is filled with and retains a gas, wherein said decellularized extracellular matrix of said organ comprises an exterior surface, and wherein said extracellular matrix including the vascular tree retain the morphology of said extracellular matrix prior to decellularization, wherein the inflated decellularized extracellular matrix of the mammalian organ or the vascularized portion thereof, or the inflated decellularized extracellular matrix of the vascularized mammalian tissue or vascularized portion thereof, has and retains a height that is increased by at least 25% relative to a corresponding uninflated decellularized extracellular matrix of the mammalian organ or the vascularized portion thereof, or the corresponding uninflated decellularized extracellular matrix of the vascularized mammalian tissue or the vascularized portion thereof.

2. The inflated decellularized extracellular matrix of claim 1 wherein said mammalian organ is a heart, a kidney, a liver, spleen, pancreas, bladder, skeletal muscle, small bowel large bowel, stomach, bone, brain, or a lung.

3. The inflated decellularized extracellular matrix of claim 1 wherein the vascularized portion is a portion of a mammalian heart, a kidney, a liver, spleen, pancreas, bladder, skeletal muscle, small bowel, large bowel stomach, bone, brain, or a lung.

4. The inflated decellularized extracellular matrix of claim 1 wherein the gas comprises air, oxygen or nitrogen.

5. The inflated decellularized extracellular matrix of claim 1 wherein the gas is a vapor.

6. The inflated decellularized extracellular matrix of claim 1 wherein the gas comprises a drug or an aerosolized drug.

7. The inflated decellularized extracellular matrix of claim 1 wherein the gas comprises one or more proteins.

8. The inflated decellularized extracellular matrix of claim 7 wherein the one or more proteins comprise a cytokine or growth factor.

9. The inflated decellularized extracellular matrix of claim 1 wherein the decellularized organ or vascularized tissue is a pig, bovine, sheep, canine or human organ or tissue.

10. An ex vivo method of inflating a decellularized extracellular matrix of a mammalian organ or a vascularized portion thereof, or a mammalian vascularized tissue or a vascularized portion thereof, comprising:
providing a decellularized extracellular matrix of a mammalian organ or a vascularized portion thereof or of a vascularized mammalian tissue or a vascularized portion thereof, wherein said extracellular matrix of said organ comprises an intact exterior surface, wherein said extracellular matrix of said organ or portion thereof, or tissue or portion thereof, comprises a vascular tree, wherein said decellularized extracellular matrix of said organ retains a majority of fluid or gas introduced to the decellularized extracellular matrix vascular tree, and wherein said organ or tissue has a substantially closed vasculature bed;
cannulating said organ or portion thereof or said tissue or portion thereof at one or more vessels, cavities and/or ducts, thereby producing a cannulated organ or portion thereof or a cannulated tissue or portion thereof, and
introducing a gas into said one or more vessels, cavities or ducts of said cannulated organ or portion thereof or cannulated tissue or portion thereof, so as to provide an inflated decellularized extracellular matrix, wherein the inflated decellularized extracellular matrix of the mammalian organ or the vascularized portion thereof, or the inflated decellularized extracellular matrix of the vascularized mammalian tissue or the vascularized portion thereof, has and retains a height that is increased by at least 25% relative to a corresponding uninflated decellularized extracellular matrix of a mammalian organ or the vascularized portion thereof, or the corresponding uninflated decellularized extracellular matrix of the vascularized mammalian tissue or vascularized portion thereof.

11. The method of claim 10 wherein the gas comprises air, nitrogen or oxygen.

12. The method of claim 10 wherein the gas comprises one or more of VEGF, FGF-2, EGF, PDGF, IGF, or HGF, or any combination thereof.

13. The method of claim 10 wherein the mammal is a human, non-human primate, bovine, porcine, canine, feline, caprine, ovine, or rodent.

14. The method of claim 10 further comprising sterilizing the inflated decellularized extracellular matrix.

15. The method of claim 10 further comprising introducing cells to at least one of the vessels, ducts or cavities.

16. The method of claim 10 wherein said mammalian organ is a heart, a kidney, a liver, spleen, pancreas, bladder, skeletal muscle, small bowel large bowel, stomach, bone, brain, or a lung.

17. A method to augment a void or treat a wound in a body cavity of a mammal, comprising administering to the void or wound the extracellular matrix of claim 1 or a portion thereof.

18. The method of claim 17 wherein the portion that is administered is granularized or morsalized.

19. The method of claim 17 wherein the extracellular matrix that is administered is cryodessicated.

20. The method of claim 17 wherein the administration is to a fistula.

21. An inflated decellularized extracellular matrix of a mammalian organ or a vascularized portion thereof, or of a vascularized mammalian tissue or vascularized portion thereof, wherein said decellularized extracellular matrix comprises a vascular tree, duct or cavity, and is filled with and retains a gas, wherein said decellularized extracellular matrix of said organ comprises an exterior surface, and wherein said extracellular matrix including the vascular tree retain the morphology of said extracellular matrix prior to decellularization, wherein the mammalian organ is a heart, a kidney, a liver, spleen, pancreas, bladder, skeletal muscle, small bowel, large bowel, stomach, bone, or brain.

* * * * *